United States Patent [19]

Carson

[11] Patent Number: 4,729,994
[45] Date of Patent: Mar. 8, 1988

[54] BENZOTHIAZEPINE VASODILATORS HAVING ARALKYL SUBSTITUTION

[75] Inventor: John R. Carson, Norristown, Pa.

[73] Assignee: McNeilab, Inc., Fort Washington, Pa.

[21] Appl. No.: 26,430

[22] Filed: Mar. 16, 1987

Related U.S. Application Data

[63] Continuation-in-part of Ser. No. 898,298, Aug. 20, 1986, abandoned.

[51] Int. Cl.$^4$ .................... A61K 31/38; C07D 285/36
[52] U.S. Cl. ........................................ 514/211; 540/491
[58] Field of Search .................... 540/491; 514/211

[56] References Cited

U.S. PATENT DOCUMENTS

| 3,562,257 | 2/1971 | Kugita et al. | 540/491 |
| 4,585,768 | 4/1986 | Takeda et al. | 514/211 |
| 4,661,635 | 4/1987 | Carson | 564/374 |

FOREIGN PATENT DOCUMENTS 0146271  6/1985  European Pat. Off. ............ 540/491

Primary Examiner—Robert T. Bond
Attorney, Agent, or Firm—David J. Levy

[57] ABSTRACT

N-Aminoalkyl 1,5-benzothiazepines of the following formula (I):

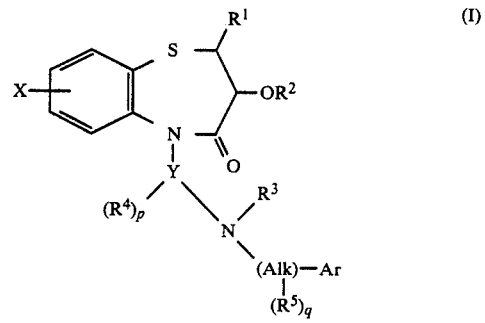

for the treatment of angina or hypertension or the prevention of heart attacks in mammals, in particular their use as coronary vasodilators.

18 Claims, No Drawings

BENZOTHIAZEPINE VASODILATORS HAVING ARALKYL SUBSTITUTION

This application is a continuation-in-part of U.S.S.N. 898,298 filed Aug. 20, 1986, now abandoned.

BACKGROUND OF THE INVENTION

Diltiazem having a chemical name of 3-(acetyloxy)-5-[2-(dimethylamino)ethyl]-2,3-dihydro-2-(4-methoxyphenyl)-1,5-benzothiazepin-4(5H)-one is a coronary vasodilator useful in the treatment of angina and has calcium blocking activity as described in U.S. Pat. No. 3,562,257. In addition, it has recently been reported by Robert S. Gibson et al. in the New England Journal of Medicine, Vol. 315, Issue #7, pages 423–429 (Aug. 14, 1986) that diltiazem prevents an often fatal second heart attack from occurring during a patient's recovery from a first heart attack. Other 1,5-benzothiazepines are disclosed in U.S. Pat. No. 4,585,768 and in published European patent application 158,340.

Other calcium blockers useful against angina are those described in my U.S. Ser. No. 665,684 filed Oct. 29, 1984 which corresponds to my published European patent application 146,271 published June 26, 1985.

It is an object of the present invention to provide calcium blockers having high levels of activity in the treatment of angina pectoris in mammals, e.g. humans, and having activity in the prevention of heart attacks in mammals, particularly the occurrence of a second heart attack by treatment of a patient during recovery from a first heart attack.

SUMMARY OF THE INVENTION

Novel benzothiazepines of the following formula (I):

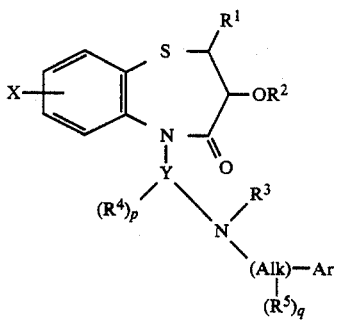

have been found to be extremely potent vasodilators as seen in the Langendorff isolated heart screen. As such, they would be considered to be useful as agents in the treatment of angina. The invention compounds may also be used in the treatment of hypertension and prevention of the reoccurrence of heart attacks in humans.

DETAILED DESCRIPTION OF THE INVENTION

Benzothiazepines of the following formula (I):

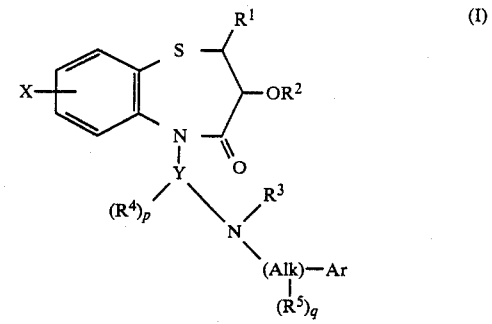

wherein
X is a hydrogen atom or a halogen atom;
$R^1$ is a phenyl ring which is unsubstituted or independently substituted by 1 to 3 of lower alkyl, lower alkoxy or halogen;
$R^2$ is a hydrogen atom or a lower alkanoyl group;
Y is a straight chain alkylene group of about 2 or 3 carbons;
$R^3$ is lower alkyl;
$R^4$ is independently lower alkyl;
p is the integer 0, 1, 2 or 3;
Alk is a straight chain alkylene of about 2 to 4 carbons;
$R^5$ is independently hydroxy, alkyl or phenyl;
q is 0, 1 or 2 or 3 if Alk is alkylene of about 2 to 4 carbons; and
Ar is a phenyl, phenoxy, thiophenoxy, naphthyl or a 5- or 6-membered heterocyclic aromatic ring which rings may be substituted independently by one or more of alkyl, alkoxy, alkylthio, hydroxy, halogen,, fluoroalkyl, nitro, amino or dialkylamino or by methylenedioxy at adjacent ring carbons,
and the pharmaceutically acceptable acid addition salts and quarternary ammonium compounds thereof.

X in more detail, is hydrogen, fluoro, chloro, bromo or iodo.
$R^1$ in more detail, is phenyl or phenyl independently substituted by 1 to 3 of methyl, ethyl, n-propyl, iso-propyl, n-butyl, sec-butyl, tert-butyl, iso-butyl, methoxy, ethoxy, n-propoxy, iso-propoxy, n-butoxy, sec-butoxy, tert-butoxy, iso-butoxy, fluoro, chloro, bromo or iodo;
$R^2$ in particular, is hydrogen, acetyl, propionyl, 2-methylpropionyl or butyryl;
Y is straight chain alkylene of 2 or 3 carbons;
$R^3$ in particular, is methyl, ethyl, n-propyl, iso-propyl, n-butyl, sec-butyl or iso-butyl;
$R^4$ in particular, is independently methyl, ethyl, n-propyl, iso-propyl, n-butyl, sec-butyl or iso-butyl;
Examples of $Y(R^4)_p$ are $-CH_2CH_2-$, $-CH(CH_3)CH_2-$ and $-CH_2CH(CH_3)$.
Alk in particular, is ethylene, trimethylene or tetramethylene, most preferably ethylene;
$R^5$ is independently hydroxy, alkyl of about 1 to 4 carbons such as methyl, ethyl or iso-propyl, or phenyl.
q in particular, is 0, 1 or 2; and
Ar is phenyl; phenoxy; thiophenoxy; naphthyl, e.g., 1- or 2-naphthyl; or a 5- or 6-membered heterocyclic aromatic ring, preferably one having 1 heteratom such as nitrogen, sulfur or oxygen, e.g. furan or thiophene attached at the 2 or 3 position, pyrrole attached at the 1, 2 or 3 position and pyridine attached at the 2, 3 or 4 position. The open positions of the ring, or rings in the case of naphthyl, of Ar may be substituted by one or more, e.g. one or two, same or different, of alkyl of about 1 to 6 carbons such as methyl or ethyl; alkoxy of about 1 to 6 carbons such as methoxy and ethoxy; alkylthio of about 1 to 6 carbons such as methylthio; hydroxy; halogen such as fluoro, chloro and bromo; fluoroalkyl of about 1 to 6 carbons and one or more fluorine atoms with examples being 2,2,2-trifluoroethyl and trifluoromethyl; nitro; amino; or dialkylamino of about 2 to 12 carbons such as dimethylamino; or methylenedioxy at adjacent ring carbons particularly if Ar is phenyl, phenoxy or thiophenoxy; e.g. 3,4-methylenedioxyphenyl.

Preferably in formula (I), the hydroxy for $R^5$ is not attached to the same carbon as the nitrogen atom in formula (I).

Particular embodiments of the present invention include compounds of formula (I) wherein
X is hydrogen;
$R^1$ is phenyl substituted by lower alkoxy;
$R^2$ is lower alkanoxy;
Y is ethylene;
$R^3$ is lower alkyl;
p is 0;
Alk is ethylene;
q is 0; and
Ar is phenyl or phenyl substituted independently by 1 or 2 of alkyl, alkoxy, alkylthio, halogen, fluoroalkyl, amino or dialkylamino or by methylenedioxy at adjacent ring carbons.

Most particularly, Ar is phenyl independently substituted by 1 or 2 of methyl, ethyl, n-propyl, iso-propyl, methoxy, ethoxy, n-propoxy, iso-propoxy, fluoro, chloro, bromo or iodo. Specific examples include 3-methoxyphenyl, 3,4-dimethoxyphenyl, 3,4-dichlorophenyl, 3,4-methylenedioxyphenyl, 3-methylphenyl, 2-methoxyphenyl, 3,5-dimethoxyphenyl and 2,3-dichlorophenyl.

Particular compounds of the inventions are:
3-(Acetyloxy)-5-[2-[[2-(3-methoxyphenyl)ethyl]methylamino]ethyl]-2,3-dihydro-2-(4-methoxyphenyl)-1,5-benzothiazepine-4(5H)-one;
3-Hydroxy-5-[2-[[2-(3-methoxyphenyl)ethyl]methylamino]ethyl]2,3-dihydro-2-(4-methoxyphenyl)-1,5-benzothiazepine-4(5H)-one;
3-(Acetyloxy)-5-[2-[[2-(3,4-dimethoxyphenyl)ethyl]methylamino]ethyl]-2,3-dihydro-2-(4-methoxyphenyl)-1,5-benzothiazepine-4(5H)-one;
3-(Hydroxy)-5-[2-[[2-(3,4-dimethoxyphenyl)ethyl]methylamino]ethyl]-2,3-dihydro-2-(4-methoxyphenyl)-1,5-benzothiazepine-4(5H)-one;
3-(Acetyloxy)-5-[2-[[2-(3,4-dichlorophenyl)ethyl]methylamino]ethyl]-2,3-dihydro-2-(4-methoxyphenyl)-1,5-benzothiazepine-4(5H)-one;
3-(Hydroxy)-5-[2-[[3,4-dichlorophenyl)ethyl]methylamino]ethyl]-2,3-dihydro-2-(4-methoxyphenyl)-1,5-benzothiazepine-4(5H)-one;
3-(Acetyloxy)-5-[2-[[2-(3,4-methylenedioxyphenyl)ethyl]methylamino]ethyl]-2,3-dihydro-2-(4-methoxyphenyl)1,5-benzothiazepine-4(5H)-one;
3-Hydroxy-5-[2-[[2-(3,4-methylenedioxyphenyl)ethyl]methylamino]ethyl]-2,3-dihydro-2-(4-methoxyphenyl)-1,5-benzothiazepine-4(5H)-one;
3-(Acetyloxy)-5-[2-[[2-(3-methylphenyl)ethyl]methylamino]ethyl]-2,3-dihydro-2-(4-methoxyphenyl)-1,5-benzothiazepine-4(5H)-one;
3-(Acetyloxy)-5-[2-[[2-methoxyphenyl)ethyl]methylamino]ethyl]-2,3-dihydro-2-(4-methoxyphenyl)1,5-benzothiazepine-4(5H)-one;
3-(Acetyloxy)-5-[2-[[2-(3,5-dimethoxyphenyl)ethyl]methylamino]ethyl]-2,3-dihydro-2-(4-methoxyphenyl)-1,5-benzothiazepine-4(5H)-one;
3-(Acetyloxy)-5-[2-[[2,3-dichlorophenyl)ethyl]methylamino]ethyl]-2,3-dihydro-2-(4-methoxyphenyl)-1,5-benzothiazepine-4(5H)-one;
3-(Acetyloxy)-5-[(S)-2-[[2-(3,4-dimethoxyphenyl)ethyl]methylamino]propyl]-2,3-dihydro-2-(4-methoxyphenyl)1,5-benzothiazepin-4(5H)-one;
3-(Acetyloxy)-5-[(S)-2-[[2-(3,4-dimethoxyphenyl)ethyl]methylamino]-1-methylethyl]-2,3-dihydro-2-(4-methoxyphenyl)-1,5-benzothiazepin-4(5H)-one;
3(Acetoxy)-5-[(S)-2-[[2-(2,3-dichlorophenyl)ethyl]methylamino]propyl]-2,3-dihydro-2-(4-methoxyphenyl)-1,5-benzothiazepin-4(5H)-one
cis-3-(acetyloxy)-5-[2-[[2-(3,4-dimethoxyphenyl)ethyl]methylamino]ethyl]-2,3-dihydro-2-(4-methoxyphenyl)1,5-benzothiazepine-4(5H)-one;
cis-3-(acetyloxy)-5-[2-[[2-(3,5-dimethoxyphenyl)ethyl]methylamino[ethyl]-2,3-dihydro-2-(4-methoxyphenyl)-1,5-benzothiazepine-4(5H)-one;
cis-3-(acetyloxy)-5-[2-[[2-(3,4-dichlorophenyl)ethyl]methylamino]ethyl]-2,3-dihydro-2-(4-methoxyphenyl)-1,5-benzothiazepine-4(5H)-one;
cis-3-(acetyloxy)-5-[2-[[2-(2,3-dichlorophenyl)ethyl]methylamino]ethyl]-2,3-dihydro-2-(4-methoxyphenyl)-1,5-benzothiazepine-4(5)-one;
cis-3-(acetyloxy)-5-[2-[[2-(3-methoxyphenyl)ethyl]methylamino]ethyl]2,3-dihydro-2,3-dihydro-2-(4-methoxyphenyl)-1,5-benzothiazepine-4(5H)-one;
cis-3-(acetyloxy)-5-[2-[[2-(3-dimethylaminophenyl)ethyl]methylamino]ethyl]-2,3-dihydro-2-(4-methoxyphenyl)-1,5-benzothiazepine-4(5H)-one;
cis-3-(acetyloxy)-5-[2-[[2-(3-trifluoromethylphenyl)ethyl]methylamino]ethyl]-2,3-dihydro-2-(4-methoxyphenyl)-1,5-benzothiazepine-4(5H)-one;
cis-3-(acetyloxy)-5-[2-[[2-(3,4-dimethoxyphenyl)-propyl]methylamino]ethyl]-2,3-dihydro-2-(4-methoxyphenyl)-1,5-benzothiazepine-4(5H)-one;
cis-5-[2-[[2-(3,4-Dimethoxyphenyl)ethyl]methylamino]ethyl]2,3-dihydro-3-hydroxy-2-(4-methoxyphenyl)-1,5-benzothiazepine-4(5H)-one; and
cis-3-(acetyloxy)-5-[2-[[2-(3,4-dimethoxyphenyl)ethyl]methylamino]propyl]-2,3-dihydro-2-(4-methoxyphenyl)1,5-benzothiazepine-4(5H)-one.

Particular Alk($R^5$)$_q$Ar groups include 3,5-dimethoxyphenyl, 2,3-dichlorophenyl, 3,4-dichlorophenyl and 3-diethylaminophenyl. Particular compounds of the invention are the benzothiazepine of the following formula (VI) and (VII):

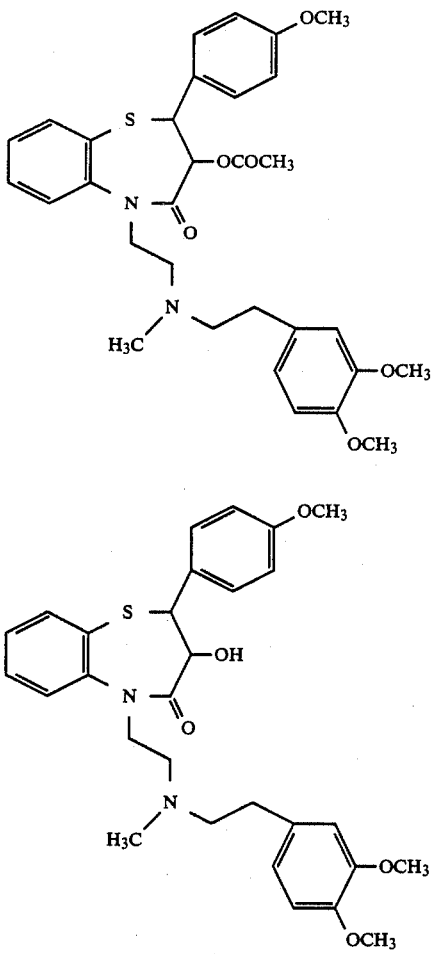

(VI)

wherein all substituents are as defined above for formula (I).

Salts, in particular, include those formed from acids such as hydrochloric, hydrobromic, hydroidic, sulfuric, phosphoric, fumaric, maleic, cyclohexylsulfamic, citric, lactic and methanesulfonic and said quaternary ammonium compounds are those formed with an alkylhalide or alkylsulfate of about 1 to 6 carbons, e.g. an alkyl bromide such as methyl iodido. Compounds of formula (I) and other compounds of the invention may exist in various isomeric forms, e.g. in view of the presence of an asymmetric carbon or by being cis or trans at the 2- and 3-positions of the benzothiazepine ring. It is understood that the present invention includes all such individual isomers and their racemates. Particular asymmetric carbons are those at the 2- and 3-positions of the thiazepine 7-membered ring. The stereochemistry at these two positions may be cis or trans.

Compounds of the present invention may be prepared by either of the following two general Reaction Schemes.

Reaction Scheme 1:

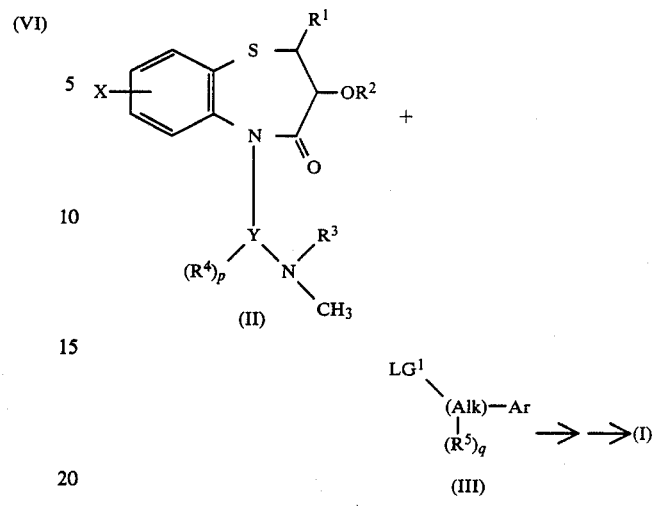

In Reaction Scheme 1, a methylamino benzothiazepine (II) is reacted with an alkylating agent of the formula (III) wherein $LG^1$ is a leaving group such as tosyl, iodo, mesyl or bromo, with X, $R^1$, $R^2$, Y, $R^3$, $R^4$, p, Alk, Ar, $R^5$ and q all as described above for (I), at about room temperature up to 150° C. to produce the quaternary ammonium salt conjugate of (II) and (III). The intermediate salt may then be reacted without isolation with a strong nucleophile such as sodium thiophenoxide as described by T. Manoharan et al. in Synthesis, page 809–812 (1983) to yield the product of formula (I).

Reaction Scheme 2:

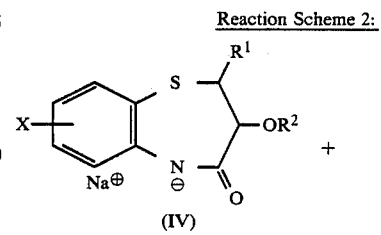

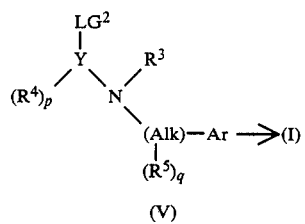

In Reaction Scheme 2, the salt (IV) is prepared as described in U.S. Pat. No. 3,562,257 at column 3. The salt (IV) is then reacted with an alkylating agent of the formula (V), wherein $LG^2$ is a leaving group such as chlorine or bromine at a temperature of about 25 to 150° C. to produce the benzothiazepine of formula (I). In formulae (IV) and (V), X, $R^1$, $R^2$, $R^3$, $R^4$, p, Y, Alk, Ar, $R^5$ and q are all as described for formula (I).

The compounds of formula (I) are useful in the treatment of the symptoms of angina pectoris by virtue of their ability to dilate coronary arteries. Their activity may be measured using the "Langendorff's isolated heart" preparation. This test has been described in "Pharmacological Experiments on Isolated Preparations". Staff of the Department of Pharmacology, University of Edinbourgh, 2nd Ed., Churchill Livingstone, N.Y. 1970, pp. 112–119. The test compounds may be administered at concentrations of 3000, 1000, 300, 100, 30, 10, 3, 1, 0.3, 0.1, 0.03 and 0.01 nanomolar ($10^{-9}$ molar).

In the Langendorff test, the known compound diltiazem was found to have a $C_{175}$ (the concentration needed to give a coronary flow of 175% of control) of 0.1 μM. In contrast, the compound of the invention prepared in Example 4 had a $C_{175}$ of 0.000126 μM.

The activity of compounds of formula (I) for the treatment of hypertension may be determined using the Spontaneously Hypertensive Rat (SHR) test as described below.

In this test, the arterial pressure of adult spontaneously hypertensive rats (Charles River) is monitored directly via an aortic cannula. The SH rats are anesthetized with an inhalation anesthetic (ether). The left carotid artery is isolated and cannulated. The tip of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. The test compounds are administered to at least 3 rats at doses selected in the range of 0.1 to 100 mg/kg of body weight by intraperitoneal (i.p.) or oral (p.o.) routes of administration. The arterial pressure and heart rate are monitored for a minimum of 24 hours. A test compound is considered to be active as an antihypertensive agent if the mean arterial pressure (MAP) indicates a fall of > 15 mm of Hg. Each animal serves as its own control.

For the treatment of hypertension, angina or the prevention of heart attacks, compounds of the present invention of the formula (I) may be administered orally or parenterally in a pharmaceutical composition comprising about 0.5 to 200 mg, preferably about 1 to 50 mg of one or more of the benzothiazepine compounds per day for an average adult human depending on the activity of the particular compound chosen. The dosage may be divided into 1 to 4 unit dosage forms per day. While the therapeutic methods of the invention are most useful for human subjects in need of alleviation of hypertension or angina, the compounds may be administered to other mammals at comparable dosages per weight of the subject.

Pharmaceutical compositions containing the benzothiazepine compounds of the present invention of formula (I), an acid addition salt thereof or a quaternary ammonium compound thereof as the active ingredient may be prepared by intimately mixing the compound with a pharmaceutical carrier according to conventional pharmaceutical compounding techniques, which carrier may take a wide variety of forms depending on the form of preparation desired for administration, e.g. oral or parenteral. In preparing the compositions in oral dosage form, any of the usual pharmaceutical media may be employed, including liquid carriers such as water, glycols, oils, alcohols and the like for oral liquid preparations such as suspensions, elixirs and solutions; and solid carriers such as starches, sugars, kaolin, calcium stearate, ethyl cellulose, etc., including materials which function as lubricants, binders, disintegrating agents and the like for powders, capsules and tablets. Because of their ease in administration, tablets and capsules represent the most advantageous oral dosage form. These compositions employ solid pharmaceutical carriers such as the aforementioned starches, sugars, kaolin and the like, generally with a lubricant such as calcium stearate. It is especially advantageous to formulate the aforementioned pharmaceutical compositions in dosage unit form for ease of administration and uniformity of dosage. The term "dosage unit form" as used in the specification and claims herein refers to physically discrete units suitable as unitary dosages, each unit containing a predetermined quantity of active ingredient calculated to produce the desire therapeutic effect in association with the required pharmaceutical carrier. Examples of such dosage unit forms are tablets, capsules, pills, powder packets, wafers, teaspoonful, tablespoonful and the like, and segregated multiples thereof.

Also part of the present invention are novel intermediates.

In the following Examples, the following abbreviations are used: E (trans); Z (cis); bp (boiling point); mp (melting point); g (grams); ml (milliliters); glc (gas liquid chromatography); hplc (high pressure liquid chromatography); M (molar); μM (micromolar); THF (tetrahydrofuran); MeOH (methanol); i-PrOH (isopropanol); DMF (dimethylformamide); EtOAc (ethyl acetate); DMSO (dimethylsulfoxide); RT (room temperature); mmoles (millimoles); mg (milligrams); mm (millimeters); hr (hours); min (minutes); and C, H, N etc. (the chemical symbols for the elements). Unless otherwise indicated, all temperatures are reported in degrees centigrade (°C.), all pressures in mm of mercury and all references to ether are to diethyl ether.

EXAMPLE 1 a. 2-(3-Methoxyphenyl)ethyl methanesulfonate

To a flask under argon was added 10.1 g (0.0661 mole) 3-methoxyphenethyl alcohol, 150 mL methylene chloride and 9.2 ml (0.0661 mole) triethylamine. The solution was cooled to 0° C. and 5.1 ml (0.0661 mole) methanesulfonyl chloride was added slowly. The reaction mixture was warmed to room temperature. After 24 hr, the reaction was washed with water and brine, and dried with $MgSO_4$. The solvent was evaporated in vacuo to give 15.0 g of the product as a clear oil.

b. 3-Methoxyphenethyl iodide

To a flask under argon was added 14.6 g (0.0634 mole) 2-(3-methoxyphenyl)ethyl methanesulfonate in 400 ml of acetone and 36.5 g (0.243 mole) of sodium iodide. The reaction mixture was refluxed for 2.5 hr. The acetone was evaporated in vacuo and the residue dissolved in ether. The ether was washed with water, sodium bicarbonate, sodium thiosulfate, water and brine, dried over $MgSO_4$, and evaporated in vacuo to give a light green oil. Distillation in a Kugelrohr apparatus gave 14.6 g of the desired product as a clear oil.

c.
cis-3-(Acetyloxy)-2,3,4,5-tetrahydro-2-(4-methoxyphenyl)-N-[2-(3-methoxyphenyl)ethyl]-N,N-dimethyl-4-oxo-1,5-benzothiazepine-5-ethanaminium iodide To a flask under argon was added 5.0 g (0.0121 mole) cis-3-(acetyloxy)-5-[2,(N,N-dimethylamino)ethyl]-2,3-dihydro-2-(4-methoxyphenyl)-1,5-benzothiazepine-4(5H)-one (diltiazem), 25 ml EtOAc, and 3.8 g (0.0145 mole) 3-methoxyphenethyl iodide. The reaction mixture was heated between 60°–65° C. for 96 hr then filtered. One recrystallization from 95% ethanol gave a 4.44 g mixture of the product and diltiazem hydroiodide as a white solid.

d. cis-3-(Acetyloxy)-5-[2-[[2-(3-methoxyphenyl)ethyl]methylamino]ethyl]-2,3-dihydro-2-(4-methoxyphenyl)-1,5-benzothiazepine-4(5H)-one (E)-Butenedioate (1:1)

To a flask under argon was added 0.77 g (0.0193 mole) of 60% NaH in oil. The NaH was washed with hexane and 50 ml of DMF was added. To the suspension was slowly added 2.0 ml (0.0193 mole) of thiophenol. The solution was stirred 5 min and 4.36 g (0.0064 mole) of crude cis-3-(acetyloxy)-2,3,4,5-tetrahydro-2-(4-methoxyphenyl)-N-[2-(3-methoxyphenyl)ethyl]-N,N-dimethyl-4-oxo-1,5-benzothiazepine-5-ethanaminium iodide added. After heating at 80° C. for 4 hr, the DMF was evaporated. The residue was dissolved in ether and washed with water, sodium bicarbonate, water and brine, dried over $K_2CO_3$ and evaporated. The residue was purified by flash chromatography, eluting with 1:50 MeOH:CHCl$_3$, to give the pure title product as a free base. Combining the product with one equivalent of fumaric acid in 2-propanol gave 2.72 g of the title compound, mp 136°–141° C.

EXAMPLE 2 cis-3-Hydroxy-5-[2-[[2-(3-methoxyphenyl)ethyl]methylamino]ethyl]2,3-dihydro-2-(4-methoxyphenyl)-1,5-benzothiazepine-4(5H)-one (E)-Butenedioate (1:1)

To a flask under argon containing 4.31 g (8.07 mmole) cis-3-(acetyloxy)-5-[2-[[3-methoxyphenyl)ethyl]methylamino]ethyl]-2,3-dihydro-2-(4-methoxyphenyl)1,5-benzothiazepine-4(5H)-one was added 35 ml methanol, the product of Example 1d, and 0.59 g (8.88 mmole) 85% KOH. After stirring at room temperature for 72 hr, the methanol was evaporated in vacuo. The residue was dissolved in ether and washed with water and brine, dried over $K_2CO_3$ and evaporated in vacuo. The residue was purified by flash chromatography, eluting with 1% methanol in chloroform. The purified residue was combined with one equivalent of fumaric acid in 2-propanol to give 3.05 g of the title product, mp 169°–171° C.

EXAMPLE 3 a. 2-(3,4-Dimethoxyphenyl)ethyl methanesulfonate

A solution of 18.2 g (0.1 mole) of 3,4-dimethoxyphenethyl alcohol in 150 ml of methylene chloride was cooled to −5° C. To the solution was added 13.9 ml (0.1 mole) of triethylamine followed by 7.7 ml (0.1 mole) of methanesulfonyl chloride keeping the temperature below 0° C. The reaction was stirred for 4 hr, poured into water, washed with brine, dried over $Na_2SO_4$, and evaporated to give 26.7 g of product as a yellow oil.

b. 3,4-Dimethoxyphenethyl iodide

To a flask was added 21.2 g (0.078 mole) of 2-(3,4-dimethoxyphenyl)ethyl methanesulfonate and 44.65 g (0.3 mole) of sodium iodide in 420 ml of acetone. The solution was refluxed for 2 hr, poured into water, washed with brine, dried over $MgSO_4$, and evaporated to give 21.1 g of a yellow oil. The oil was recrystallized in MeOH to give 17.1 g of product, mp 43°–46° C.

c. cis-3-(Acetyloxy)-2,3,4,5-tetrahydro-2-(4-methoxyphenyl)-N-[2-(3,4-dimethoxyphenyl)ethyl]N,N-dimethyl-4-oxo-1,5-benzothiazepine-5-ethanaminium iodide To a flask under argon containing 4.94 g (0.0119 mole) diltiazem was added 50 ml ethyl acetate and 3.48 g (0.0119 mole) 3,4-dimethoxyphenethyl iodide. The reaction was refluxed for 24 hr then filtered. The filtrate was washed with sodium bicarbonate and brine, dried over $K_2CO_3$, and 0.85 g 3,4-dimethoxyphenethyl iodide added and the reaction refluxed for 18 hr then filtered. The last step was repeated but 1.75 g of 3,4-dimethoxyphenethyl iodide was added and the reaction refluxed 5 hr. The filtered materials were combined and recrystallized from 95% ethanol to give a mixture of product and diltiazem hydroiodide.

d. cis-3-(Acetyloxy)-5-[2-[[2-(3,4-dimethoxyphenyl)ethyl]methylamino]ethyl]-2,3-dihydro-2-(4-methoxyphenyl)-1,5-benzothiazepine-4(5H)-one Hydrochloride Hydrate (2:2:1)

Using the method of Example 1d, but substituting cis-3-(acetyloxy)-2,3,4,5-tetrahydro-2-(4-methoxyphenyl)-N-[2-(3,4-dimethoxyphenyl)ethyl]-N,N-dimethyl-4-oxo-1,5-benzothiazepine-5-ethanaminium methanesulfonate for cis-3-(acetyloxy)-2,3,4,5-tetrahydro-2-(4-methoxyphenyl)-N-[2-(3-methoxyphenyl)ethyl]-N,N-dimethyl-4-oxo-1,5-benzothiazepine-5-ethanaminium iodide and using preparative hplc (1:3 acetone:hexane) for purification, product was obtained in 18% yield by precipitating from ethereal hydrogen chloride, mp 117°–118° C.

EXAMPLE 4 cis-3-(Hydroxy)-5-[2-[[2-(3,4-dimethoxyphenyl)ethyl]methylamino]ethyl]-2,3-dihydro-2-(4-methoxyphenyl)-1,5-benzothiazepine-4(5H)-one Hydrochloride Hydrate (2:2:1)

Using the method of Example 2, but substituting cis-3-(acetyloxy)-5-[2-[[2-(3,4-dimethoxyphenyl)ethyl]methylamino]ethyl]-2,3-dihydro-2-(4-methoxyphenyl)-1,5-benzothiazepine-4(5H)-one for cis-3-(acetyloxy)5-[2-[[2-(3-methoxyphenyl)ethyl]methylamino]ethyl]-2,3-dihydro-2-(4-methoxyphenyl)-1,5-benzothiazepine-4(5H)-one, the title product was obtained in 57% yield by precipitation from ethereal hydrogen chloride after purification by preparation hplc (1:3 acetone:hexane), mp 110°–115° C.

EXAMPLE 5 a. 2-(3,4-Dichlorophenyl)ethyl methansulfonate

Using the method of Example 1a, but substituting 3,4-dichlorophenethyl alcohol for 3-methoxyphenethyl alcohol, the title product was obtained as a yellow oil in 88% yield.

b. 3,4-dichlorophenethyl iodide

Using the method of Example 1b, but substituting 2-(3,4-dichlorophenyl)ethyl methanesulfonate for 2-(3-methoxyphenyl)ethyl methanesulfonate and refluxing the reaction for 24 hr, the title product was obtained as a yellow oil in 96% yield.

c.
cis-3-(Acetyloxy)-2,3,4,5-tetrahydro-2-(4-methoxyphenyl)-N-[2-(3,4-dichlorophenyl)ethyl]-N,N-dimethyl-4-oxo-1,5-benzothiazepine-5-ethanaminium iodide Using the method of Example 1c, but substituting 3,4-dichlorophenethyl iodide for 3-methoxyphenethyl iodide, heating to 58° C. for 72 hr, and evaporating the ethyl acetate, the product mixture was crystallized from ether as a yellow solid.

d.
cis-3-(Acetyloxy)-5-[2-[[2-(3,4-dichlorophenyl)ethyl]methylamino]ethyl]-2,3-dihydro-2-(4-methoxyphenyl)-1,5-benzothiazepine-4(5H)-one (E)-Butenedioate (1:1)

Using the method of Example 1d, but substituting cis-3-(acetyloxy)-2,3,4,5-tetrahydro-2-(4-methoxyphenyl)-N-[2-(3,4-dichlorophenyl)ethyl]-N,N-dimethyl-4-oxo-1,5-benzothiazepine-5-ethanaminium iodide for cis-3-(acetyloxy)-2,3,4,5-tetrahydro-2-(4-methoxyphenyl)-N-[2-(3-methoxyphenyl)ethyl]-N,N-dimethyl-4-oxo-1,5-benzothiazepine-5-ethanaminium iodide, the title product was obtained in 22% yield, mp 152°–154° C.

EXAMPLE 6 cis-3-(Hydroxy)-5-[2-[[3,4-dichlorophenyl)ethyl]methylamino]ethyl]-2,3-dihydro-2-(4-methoxyphenyl)-1,5-benzothiazepine-4(5H)-one (E)-Butenedioate (1:1)

Using the method of Example 2, but substituting cis-3-(acetyloxy)-5-[2-[[2-(3,4-dichlorophenyl)ethyl]methylamino]ethyl]-2,3-dihydro-2-(4-methoxyphenyl)-1,5-benzothiazepine-4(5H)-one for cis-3-(acetyloxy)-5-[2-[[2-(3-methoxyphenyl)ethyl]methylamino]ethyl]-2,3-dihydro-2-(4-methoxyphenyl)-1,5-benzothiazepine-4(5H)-one, the title product was obtained in 75% yield, mp 126°–129° C.

EXAMPLE 7 a. 2-(3,4-methylenedioxyphenyl)ethyl methanesulfonate

Using the method of Example 1a, but substituting 3,4-methylenedioxyphenethyl alcohol for 3-methoxyphenethyl alcohol and stirring for 4 hr at 0° C., the title product was obtained as a clear oil in 95% yield.

b. 3,4-Methylenedioxyphenethyl iodide

Using the method of Example 1b, but substituting 2-(3,4-methylenedioxyphenyl)ethyl methanesulfonate for 2-(3-methoxyphenyl)ethyl methanesulfonate, refluxing the reaction for only 2 hr and recrystallizing in 95% ethanol instead of distilling, the product was obtained in 64% yield, mp 36°–38° C.

c. cis-3-(Acetyloxy)-2,3,4,5-tetrahydro-2-(4-methoxyphenyl)-N-[2-(3,4-methylenedioxyphenyl)ethyl]-N,N-dimethyl-4-oxo-1,5-benzothiazepine-5-ethanaminium iodide Using the method of Example 1c, but substituting 3,4-methylenedioxyphenethyl iodide for 3-methoxyphenethyl iodide, stirring at room temperature for 72 hr followed by heating at 50° C. for 48 hr, and decanting the solvent, the product mixture was obtained as an oil.

d.
cis-3-(Acetyloxy)-5-[2-[[2-(3,4-methylenedioxyphenyl)ethyl]methylamino]ethyl]-2,3-dihydro-2-(4-methoxyphenyl)-1,5-benzothiazepine-4(5H)-one (E)-Butenedioate (1:1)

Using the method of Example 1d, but substituting cis-3-(acetyloxy)-2,3,4,5-tetrahydro-2-(4-methoxyphenyl)-N-[2,(3,4-methylenedioxyphenyl)ethyl]-N,N-dimethyl-4-oxo-1,5-benzothiazepine-5-ethanaminium iodide for cis-3-(acetyloxy)-2,3,4,5-tetrahydro-2-(4-methoxyphenyl)-N-[2-(3-methoxyphenyl)ethyl]-N,N-dimethyl-4-oxo-1,5-benzothiazepine-5-ethanaminium iodide, product was obtained in 30% yield, mp 158°–160° C.

EXAMPLE 8 cis-3-Hydroxy-5-[2-[[2-(3,4-methylenedioxyphenyl)ethyl]methylamino]ethyl]-2,3-dihydro-2-(4-methoxyphenyl)-1,5-benzothiazepine-4(5H)-one In a manner similar to the procedure of Example 2, the title product may be obtained utilizing the 3-Acetyloxy starting material of Example 7d.

EXAMPLE 9 a. 2-(3-Methylphenyl)ethyl methansulfonate

Using the method of Example 1a, but substituting 3-methylphenethyl alcohol for 3-methoxyphenethyl alcohol, the title product was obtained in 95% yield.

b. 3-Methylphenethyl iodide

Using the method of Example 1b, but substituting 2-(3-methylphenyl)ethyl methanesulfonate for 2-(3-methoxyphenyl)ethyl methanesulfonate and refluxing for 2 hr, the title product was obtained as a clear oil in 74% yield.

c. cis-3-(Acetyloxy)-2,3,4,5-tetrahydro-2-(4-methoxyphenyl)-N-[2-(3-methylphenyl)ethyl]-N,N-dimethyl-4-oxo-1,5-benzothiazepine-5-ethanaminium iodide Using the method of Example 1c, but substituting 3-methylphenethyl iodide for 3-methoxyphenethyl iodide, heating at 65° C. for 72 hr, and decanting the solvent, the product mixture was obtained as an oil.

d.
cis-3-(Acetyloxy)-5-[2-[[2-(3-methylphenyl)ethyl]methylamino]ethyl]-2,3-dihydro-2-(4-methoxyphenyl)-1,5-benzothiazepine-4(5H)-one (E)-Butenedioate (1:1)

Using the method of Example 1d, but substituting cis-3-(acetyloxy)-2,3,4,5-tetrahydro-2-(4-methoxyphenyl)-N-[2-(3-methylphenyl)ethyl]-N,N-dimethyl-4-oxo-1,5-benzothiazepine-5-ethanaminium iodide for cis-3-(acetyloxy)-2,3,4,5-tetrahydro-2-(4-methoxyphenyl)-N-[2-(3-methoxyphenyl)ethyl]-N,N-dimethyl-4-oxo-1,5-benzothiazepine-5-ethanaminium iodide, the title product was obtained in 33% yield, mp 152°–154° C.

EXAMPLE 10 a. 2-(2-Methoxyphenyl)ethyl methanesulfonate

Using the method of Example 1a, but substituting 2-methoxyphenethyl alcohol for 3-methoxyphenethyl alcohol, the title product was obtained in 96% yield.

b. 2-Methoxyphenethyl iodide

Using the method of Example 1b, but substituting 2-(2-methoxyphenyl)ethyl methanesulfonate for 2-(3-methoxyphenyl)ethyl methansulfonate and refluxing the reaction for 24 hr, the title product was obtained in 88% yield.

c. cis-3-(Acetyloxy)-2,3,4,5-tetrahydro-2-(4-methoxyphenyl)-N-[2-(2-methoxyphenyl)ethyl]-N,N-dimethyl-4-oxo-1,5-benzothiazepine-5-ethanaminium iodide The method of Example 1c was used substituting 2-methoxyphenethyl iodide for 3-methoxyphenethyl iodide. The reaction was heated at 65° C. for 72 hr then filtered to give the title product.

d. cis-3-(Acetyloxy)-5-[2-[[2-methoxyphenyl)ethyl]methylamino]ethyl]-2,3-dihydro-2-(4-methoxyphenyl)1,5-benzothiazepine-4(5H)-one (E)-Butenedioate (1:1)

Using the method of Example 1d, but substituting cis-3-(acetyloxy)-2,3,4,5-tetrahydro-2-(4-methoxyphenyl)-N-[2-(2-methoxyphenyl)ethyl]-N,N-dimethyl-4-oxo-1,5-benzothiazepine-5-ethanaminium iodide for cis-3-(acetyloxy)-2,3,4,5-tetrahydro-2-(4-methoxyphenyl)-N-[2-(3-methoxyphenyl)ethyl]-N,N-dimethyl-4-oxo-1,5-benzothiazepine-5-ethanaminium iodide, the title product was obtained in 40% yield, mp 159°–161° C.

EXAMPLE 11 a. 2-(3,5-Dimethoxyphenyl)ethyl methansulfonate

Using the method of Example 1a, but substituting 3,5-dimethoxyphenethyl alcohol for 3-methoxyphenethyl alcohol and reacting to 0° C. for 6 hr, the title product was obtained as a yellow oil in 100% yield.

b. 3,5-Dimethoxyphenethyl iodide

Using the method of Example 1b, but substituting 2-(3,5-dimethoxyphenyl)ethyl methanesulfonate for 2-(3-methoxyphenyl)ethyl methanesulfonate and refluxing for 2 hr, the title product was obtained in 77% yield as a yellow solid, mp 30°–33° C.

c. cis-3-(Acetyloxy)-2,3,4,5-tetrahydro-2-(4-methoxyphenyl)-N-[2-(3,5-dimethoxyphenyl)ethyl]-N,N-dimethyl-4-oxo-1,5-benzothiazepine-5-ethanaminium iodide To a flask under nitrogen was added 5.0 g (0.0121 mole) of diltiazem, 3.52 g (0.0121 mole) of 3,5-dimethoxyphenethyl iodide, and 20 ml of EtOAc. The reaction mixture was heated at 50° C. for 24 hr then at 75° C. for 97 hr. The reaction was cooled to RT, the solvent decanted, and the oily residue washed three times with EtOAc. The oily residue was dissolved in methylene chloride, washed with water and dried over MgSO4. The solvent was evaporated to give 5.45 g of a mixture of the title product and diltiazem hydroiodide as a tan foam.

d. cis-3-(Acetyloxy)-5-[2-[[2-(3,5-dimethoxyphenyl)ethyl]-methylamino]ethyl]-2,3-dihydro-2-(4-methoxyphenyl)-1,5-benzothiazepine-4(5H)-one (E)-Butenedioate (1:1)

Using the method of Example 1d, but substituting cis-3-(acetyloxy)-2,3,4,5-tetrahydro-2-(4-methoxyphenyl)-N-[2-(3,5-dimethoxyphenyl)ethyl]-N,N-dimethyl-4-oxo-1,5-benzothiazepine-5-ethanaminium iodide for cis-3-(acetyloxy)-2,3,4,5-tetrahydro-2-(4-methoxyphenyl)-N[2-(3-methoxyphenyl)ethyl]-N,N-dimethyl-4-oxo-1,5-benzothiazepine-5-ethanaminium iodide and heating for 6 hr, product was obtained in 13% yield after recrystallizing from MeOH/i-PrOH, mp 179°–181° C.

EXAMPLE 12 a. 2-(2,3-Dichlorophenyl)ethyl methansulfonate

Using the method of Example 1a, but substituting 2,3-dichlorphenethyl alcohol for 3-methoxyphenethyl alcohol and reacting at 0° C. for 4 hr, the title product was obtained as a yellow oil in 100% yield.

b. 2,3-Dichlorophenethyl iodide

Using the method of Example 1b, but substituting 2-(2,3-dichlorophenyl)ethyl methanesulfonate for 2-(3-methoxyphenyl)ethyl methanesulfonate and refluxing for 3 hr, the title product was obtained as a yellow oil in 67% yield.

c. cis-3-(Acetyloxy)-2,3,4,5-tetrahydro-2-(4-methoxyphenyl)-N-[2-(2,3-dichlorophenyl)ethyl]-N,N-dimethyl-4-oxo-1,5-benzothiazepine-5-ethanaminium iodide Using the method of Example 1c, but substituting 2,3-dichlorophenethyl iodide for 3-methoxyphenethyl iodide and heating at 70° C. for 96 hr, the title product was obtained as an off-white solid.

d. cis-3-(Acetyloxy)-5-[2-[[2,3-dichlorophenyl)ethyl]methylamino]ethyl]-2,3-dihydro-2-(4-methoxyphenyl)-1,5-benzothiazepine-4(5H)-one (E)-Butenedioate (1:1)

Using the method of Example 1d, but substituting cis-3-(acetyloxy)2,3,4,5-tetrahydro-2-(4-methoxyphenyl)-N-[2-(2,3-dichlorophenyl)ethyl]-N,N-dimethyl-4-oxo-1,5-benzothiazepine-5-ethanaminium iodide for cis-3-(acetyloxy)-2,3,4,5-tetrahydro-2-(4-methoxyphenyl)-N-[2-(3-methoxyphenyl)ethyl]-N,N-dimethyl-4-oxo-1,5-benzothiazepine-5-ethanaminium iodide, product was obtained in 14% yield, mp 145°–147° C.

EXAMPLE 13 a. (S)-N-(2-Hydroxy-1-methylethyl)-3,4-dimethoxybenzeneacetamide

Into a Morton flask was placed 10 g (0.137 mole) of (S)-(=)-2-amino-1-propanol in 200 mL of chloroform. To this was added 137 ml (0.137 mole) of 1N sodium hydroxide. To this mixture was added over 1 hr a solution of 29.4 g (0.137 mole) of 3,4-dimethoxyphenylacetyl chloride in 100 ml of chloroform. The reaction mixture was stirred vigorously for 4 hr. The organics were separated, washed with water, brine and dried (K2CO3). The solvent was evaporated in vacuo and the residue was recrystallized from ETOAc to give 22.14 g of (S)-N-(2-hydroxy-1-methylethyl)-3,4-dimethoxybenzeneacetamide (64% yield), mp 122°–125° C.

b.
(S)-2-[[2-(3,4-Dimethoxyphenyl)ethyl]amino]-1-propanol

To a suspension of 12.6 g (0.33 mole) lithium aluminum hydride (LAH) in 150 mL of dry THF under argon was added dropwise a suspension of 21.0 g (0.083 mole) (S)-N-(2-hydroxy-1-methylethyl)-3,4-dimethoxybenzeneacetamide in dry THF. The reaction mixture was heated under reflux for 4 hr. An additional 1.0 g of LAH was added and refluxed another 3 hr. An additional 3.0 g of LAH was added and the reaction was refluxed overnight. To the reaction was added 69 mL (0.48 mole) of triethanolamine over 1 hr. After stirring for 90 min, 16 ml of water was added and this was stirred overnight. An additional 12 ml of water was added. The solid that formed was filtered off and the filter cake was washed three times with ether and once with THF. The filtrate was washed with brine and dried ($K_2CO_3$). The solvent was removed in vacuo. The residue was dissolved in ether/acetonitrile, the undissolved solid was filtered off and the filtrate was evaporated in vacuo. The residue was treated with ethereal hydrogen chloride and the solid was collected. Three recrystallizations from acetonitrile gave 6.9 g of (S)-2-[[2-(3,4-dimethoxyphenyl)ethyl]amino]-1-propanol (38%) mp, 120°-123° C.

c.
(S)-2-[[2-(3,4-Dimethoxyphenyl)ethyl]methylamino]-1-propanol

To a solution of 6.25 g of (0.026 mole) (S)-2-[[2-(3,4-dimethoxyphenyl)ethyl]amino]-1-propanol in 50 ml of MeOH under argon was added 3.9 ml (0.052 mole) of 37% aqueous formaldehyde and 4.7 g of sodiumborohydride pellets added one at a time. The solution was stirred at RT for 24 hr. an additional 1.0 ml of 37% aqueous formaldehyde and 1.0 g of sodium borohydride were added and the solution stirred for an additional 2.5 hr. Enough glacial acetic acid was added to react with the sodium borohydride. The reaction was made basic by addition of 3N sodium hydroxide. The methanol was evaporated in vacuo and the residue was extracted three times with ether. The organics were washed with brine an dried ($K_2CO_3$). Evaporation of the solvent in vacuo gave 5.74 g of (S)-2-[[2-(3,4-dimethoxyphenyl)ethyl]methylamino]-1-propanol as an oil (87% yield).

d.
(S)-N-(2-Chloro-1-methylethyl)-3,4-dimethoxy-N-methylbenzeneethanamine Hydrochloride To a solution of 7.06 g (0.028 mole) of (S)-2-[[2-(3,4-dimethoxyphenyl)ethyl]methylamino]-1-propanol hydrochloride in 100 ml of chloroform was added 4.8 ml (0.067 mole) of thionyl chloride and the reaction was heated to reflux for 3 hr. The reaction was cooled and the solvent was evaporated in vacuo to give 3.09 g of (S)-N-(2-chloro-1-methylethyl)-3,4-dimethoxy-N-methylbenzeneethanamine hydrochloride as a brown glass (43%).

e.
cis-3-(Acetyloxy)-5-[(S)-2-[[2-(3,4-dimethoxyphenyl)ethyl]methylamino]propyl]-2,3-dihydro-2-(4-methoxyphenyl)-1,5-benzothiazepin-4(5H)-one Dry silica gel 1.32 g, 2.75 g (0.008 mole) of 2-(4'-methoxyphenyl)-3-acetoxy-2,3-dihydro-1,5-benzothiazepine-4(5H)-one, 28 mL of Aldrich gold label grade DMSO, and 0.39 g (0.0096 mole) of 60% sodium hydride in oil, was stirred for 1 hr, and 3.21 g (0.0096 mole) of (S)-N-(2-chloro-1-methylethyl)-3,4-dimethoxy-N-methylbenzeneethaneamine in dry ether was added. The reaction was stirred at RT for 5 hr. Glacial acetic acid was added until pH 6 and the reaction was stirred for 10 min. The reaction was extracted three times with $CH_2Cl_2$, the organics were combined, washed with water, brine and dried ($Na_2SO_4$). The solvent was evaporated in vacuo. The residue was flashed chromatographed on silica gel using 1:1 EtOAc:hexane as the elutant. The isolated material was treated with ethereal hydrogen chloride to give 2.24 g of the title product as the hydrochloride (50% yield), mp 147°-150° C.

EXAMPLE 14
cis-3-(Acetyloxy)-5-[(S)-2-[[2-(3,4-dimethoxyphenyl)ethyl]methylamino]-1-methylethyl]-2,3-dihydro-2-(4-methoxyphenyl)-1,5-benzothiazepin-4(5H)-one Hydrochloride From the chromatography in Example 13C, a separate fraction was also isolated. This was treated with ethereal hydrogen chloride to give 0.14 g of the title compound (3% yield), mp 125°-128° C.

EXAMPLE 15
a. 1,2-Dichloro-3-(2-methoxyethenyl)benzene

Into a flask under argon containing 700 ml of dry THF was placed 159 g (0.47 mole) of methyl(triphenylphosphoranylidene)acetate. To the stirred suspension cooled in an ice/water bath was added dropwise 320 ml (0.47 mole) of 1.45M n-butyllithium in hexane. After stirring for 20 min, 74 g (0.42 mole) of 2,3-dichlorobenzaldehyde in 700 ml of dry THF was added. After 2 hr the reaction mixture was washed with an ammonium chloride solution, brine and dried ($MgSO_4$). The solvent was evaporated in vacuo. The residue was taken up in ether, the undissolved solid was filtered off, and the solvent was evaporated in vacuo. The residue was distilled in a Kugelrohr apparatus at 0.005 mm Hg and the fraction distilling between 80°-100° C. collected. The distillate was distilled at 0.005 mm Hg using a Vigro column and the product collected between 101°-116° C. A preparative hplc on silica gel using hexane as the elutant gave 28.02 g of the title compound as an oil (33%).

b. 2,3-Dichlorobenzeneacetaldehyde

To a solution of 15.0 g (0.074 mole) 1,2-dichloro-3-(2-methoxyethenyl)benzene in 150 ml of THF was added 15 ml of 35% perchloric acid in water. The reaction was refluxed for 3.5 hr then poured into ice/water. The aqueous layer was extracted two times with ether, the organics were washed with water, brine and dried ($MgSO_4$). Evaporation of the solvent gave 13.91 g of crude 2,3-dichlorobenzeneacetaldehyde a yellow oil (99%).

c. (S)-2-[[2-(2,3-Dichlorophenyl)ethyl]amino]-1-propanol Hydrogenchloride

To a solution of 13.0 g (0.074 mole) of crude 2,3-dichlorobenzeneacetaldehyde in 50 ml of MeOH was added 5.7 ml (0.074 mole) of (S)-2-amino-1-propanol. The reaction was placed under an atmosphere of argon and 3.6 g (0.058 mole) of sodium cyanoborohydride was added. After stirring for 2.5 hr, the reaction was made acidic by adding ethereal hydrogen chloride. After stirring of 30 min enough 3N sodium hydroxide was added to make the reaction basic. The reaction mixture was extracted with ether and the ether layer was washed with water, brine and dried (K₂CO₃). Evaporation of the solvent in vacuo gave a yellow oil. The oil was treated with ethereal hydrogen chloride and the solid was collected. The solid was recrystallized from 2-propanol to give 5.10 g of the title compound (28% yield), mp 148°-151° C.

d.
(S)-2-[[2-(2,3-dichlorophenyl)ethyl]methylamino]-1-propanol Hydrochloride

According to the procedure in Example 13c, the title compound was prepared (77% yield) mp 94°-97° C.

e.
(S)-2,3-dichloro-N-(2-chloro-1-methylethyl)-N-methyl-benzeneethaneamine Hydrochloride According to the method in Example 13d, the title compound was prepared (96.5% yield), mp 157°-158° C.

f.
cis-3-(Acetoxy)-5-[(S)-2-[[2-(2,3-dichlorophenyl)ethyl]methylamino]propyl]-2,3-dihydro-2-(4-methoxyphenyl)-1,5-benzothiazepin-4(5H)-one By the procedure of Example 3c and employing (S)-2,3-dichloro-N-(2-chloro-1-methylethyl)-N-methylbenzeneethaneamine in place of (S)-N-(2-chloro-1-methylethyl)-3,4-dimethoxy-N-methylbenzeneethaneamine, the title compound was obtained, m/e=587 by mass spectrometry.

EXAMPLE 16 cis-3-(Acetyloxy)-5-[2-[[2-(3,4-dimethoxyphenyl)ethyl]methylamino]ethyl]-2,3-dihydro-2-(4-methoxyphenyl)-1,5-benzothiazepine-4(5H)-one Hydrochloride Hydrate Formula (I): X=H; R¹=4—OCH₃phenyl; R²=—COCH₃; Y=—CH₂CH₂—; R³—CH₃; p=0; Alk=—CH₂CH₂—; q=0; Ar=3,4-di—OCH₃phenyl.

To a solution of 6.5 g (0.0157 mole) cis-3-(acetyloxy)5-[2-(N,N-dimethylamino)ethyl]-2,3-dihydro-2-(4-methoxyphenyl)-1,5-benzothiazepine-4(5H)-one, known as diltiazem, in 25 mL of dry DMF was added 3.8 g (0.0172 mole) 3,4-dimethoxyphenethylbromide. The solution was heated to 100° C. for 10 hr then left to stir at room temperature for 60 hr. An additional 1.9 g (0.00775 mole) of the bromide was added. The reaction was heated for 35 hr at 100° C. at which point the quaternary salt formation was complete.

To 1.05 g (0.0157 mole) of NaH in 10 mL of dry DMF was added 4.81 mL (0.0157 mole) thiophenol. After stirring for 20 min at room temperature the reaction mixture containing the quaternary salt was added and the resulting solution was heated to 80° C. for 4 hr. The reaction mixture was cooled and the solvent was concentrated in vacuo. The residue was partitioned between ether and aqueous NaHCO₃. The aqueous layer was again extracted with ether and the ether layers were combined, washed with H₂O, NaHCO₃, brine and dried (K₂CO₃). The ether was evaporated in vacuo to give 11.03 g of a yellow oil. Flash chromatography with silica gel was performed twice on the oil first eluting with 1:1 acetone:hexane then 1:3 acetone:hexane. Fractions containing the desired product were concentrated in vacuo. To the resulting oil was added ethereal HCl to give 0.600 g of cis-3-(acetyloxy)-5-[2[[2-(3,4-dimethoxyphenyl)ethyl]methylamino]ethyl]-2,3-dihydro-2-(4-methoxyphenyl)-1,5-benzothiazepine-4(5H)-one hydrochloride hydrate; mp 118°-122° C.; yield 6.8%.

EXAMPLES 17-22

Using the procedures of Example 16 and substituting the appropriate compounds of formula (III) in the place of 3,4-dimethoxyphenethylbromide, the following compounds may be obtained:

cis-3-(acetyloxy)-5-[2-[[2-(3,5-dimethoxyphenyl)ethyl]methylamino]ethyl]-2,3-dihydro-2-(4-methoxyphenyl)-1,5-benzothiazepine-4(5H)-one;

cis-3-(acetyloxy)-5-[2-[[2-(3,4-dichlorophenyl)ethyl]methylamino]ethyl]-2,3-dihydro-2-(4-methoxyphenyl)-1,5-benzothiazepine-4(5H)-one;

cis-3-(acetyloxy)-5-[2-[[2-(2,3-dichlorophenyl)ethyl]methylamino]ethyl]-2,3-dihydro-2-(4-methoxyphenyl)-1,5-benzothiazepine-4(5H)-one;

cis-3-(acetyloxy)-5-[2-[[2-(3-methoxyphenyl)ethyl]methylamino]ethyl]-2,3-dihydro-2-(4-methoxyphenyl)-1,5-benzothiazepine-4(5H)-one;

cis-3-(acetyloxy)-5-[2-[[2-(3-trifluoromethylphenyl)ethyl]methylamino]ethyl]-2,3-dihydro-2-(4-methoxyphenyl)-1,5-benzothiazepine-4(5H)-one; and cis-3-(acetyloxy)-5-[2-[[2-(3,4-dimethoxyphenyl)propyl]methylamino]ethyl]-2,3-dihydro-2-(4-methoxyphenyl)-1,5-benzothiazepine-4(5H)-one.

EXAMPLE 23 cis-5-[2-[[2-(3,4-Dimethoxyphenyl)ethyl]methylamino]ethyl]-2,3-dihydro-3-hydroxy-2-(4-methoxyphenyl)-1,5benzothiazepine-4(5H)-one The product of Example 16 may be hydrolyzed with sodium hydroxide to produce the title compound. Alternatively, the benzothiazepine starting material in Example 16 may be 2-(4-methoxyphenyl)-3-hydroxy-5-(β-dimethylaminoethyl)-2,3-dihydro-1,5-benzothiazepine-4(5H)-one as described in U.S. Pat. No. 3,562,257 whereby the title compound will be produced.

What is claimed is:

1. A benzothiazepine of the following formula (I):

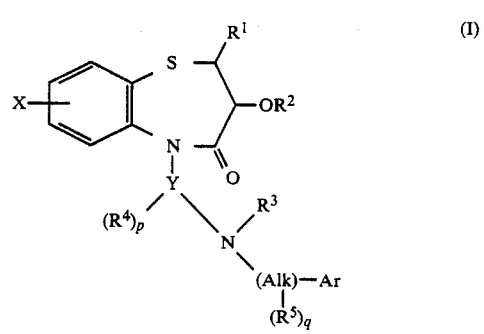

wherein

X is a hydrogen atom or a halogen atom;

R¹ is a phenyl ring which is unsubstituted or independently substituted by 1 to 3 of lower alkyl, lower alkoxy or halogen;

R² is a hydrogen atom or a lower alkanoyl group;

Y is a straight chain alkylene group of about 2 or 3 carbons;

$R^3$ is lower alkyl;
$R^4$ is independently lower alkyl;
p is the integer 0, 1, 2 or 3;
Alk is a straight chain alkylene of about 2 to 4 carbons;
$R^5$ is independently hydroxy, alkyl or phenyl;
q is 0, 1 or 2 or 3 if Alk is alkylene of about 2 to 4 carbons; and
Ar is a phenyl, phenoxy, thiophenoxy, naphthyl or a 5- or 6-membered heterocyclic aromatic ring which rings may be substituted independently by one or more of alkyl, alkoxy, alkylthio, hydroxy, halogen, fluoroalkyl, nitro, amino or dialkylamino or by methylenedioxy at adjacent ring carbon, and the pharmaceutically acceptable acid addition salts and quaternary ammonium compounds thereof.

2. The benzothiazepine of claim 1, wherein
$X_1$ is hydrogen, fluoro, chloro, bromo or iodo;
$R^1$ is phenyl or phenyl independently substituted by 1 to 3 of methyl, ethyl, n-propyl, isopropyl, n-butyl, sec-butyl, tert-butyl, iso-butyl, methoxy, ethoxy, n-propoxy, iso-propoxy, n-butoxy, sec-butoxy, tert-butoxy, iso-butoxy, fluoro, chloro, bromo or iodo;
$R^2$ is hydrogen, acetyl, propionyl, 2-methyl-propionyl or butryl;
Y is straight chain alkylene of 2 or 3 carbons;
$R^3$ is methyl, ethyl, n-propyl, iso-propyl, n-butyl, sec-butyl or iso-butyl;
$R^4$ is independently methyl, ethyl, n-propyl, iso-propyl, n-butyl, sec-butyl or iso-butyl;
p is 0, 1, 2 or 3;
Alk is ethylene, trimethylene or tetramethylene;
$R^5$ is hydroxy, alkyl of about 1 to 4 carbons or phenyl;
q is 0, 1 or 2; and
Ar is phenyl, phenoxy, thiophenoxy, naphthyl or a 5- or 6-membered heterocyclic aromatic ring having one nitrogen, sulfur or oxygen atom which rings may be substituted by one or more of alkyl, alkoxy or alkylthio of about 1 to 6 carbons each, hydroxy, fluoro, chloro, bromo, fluoroalkyl of about 1 to 6 carbons, nitro, amino, dialkylamino of about 2 to 12 carbons or methylenedioxy.

3. The benzothiazepine of claim 1, wherein said pharmaceutically acceptable acid addition salts are formed from acids selected from the group consisting of hydrochloric, hydrobromic, hydroiodic, sulfuric, phosphoric, fumaric, maleic, cyclohexylsulfamic, citric, lactic and methanesulfonic and said quaternary ammonium compounds are those formed with an alkylhalide or alkylsulfate.

4. The benzothiazepine of claim 1, wherein X is hydrogen.

5. The benzothiazepine of claim 1, wherein Alk is straight chain alkylene of 2 to 3 carbons.

6. The benzothiazepine of claim 1, wherein Alk is ethylene.

7. The benzothiazepine of claim 1, wherein
X is hydrogen;
$R^1$ is phenyl substituted by lower alkanoyl;
$R^2$ is lower alkanoxy;
Y is ethylene;
$R^3$ is lower alkyl;
p is 0;
Alk is ethylene;
q is 0; and
Ar is phenyl or phenyl substituted independently by 1 or 2 of alkyl, alkoxy, alkylthio, hydroxy, halogen, fluoroalkyl, nitro, amino or dialkylamino or by methylene dioxy at adjacent ring carbons.

8. The benzothiazepine of claim 5, wherein Ar is phenyl independently substituted by 1 or 2 of methyl, ethyl, n-propyl, iso-propyl, methoxy, ethoxy, n-propoxy, iso-propoxy, fluoro, chloro, bromo or iodo.

9. The benzothiazepine of claim 1, wherein said benzothiazepine is:
3-hydroxy-5-[2-[[2-(3-methoxyphenyl)ethyl]methylamino]ethyl]-2,3-dihydro-2-(4-methoxyphenyl)-1,5-benzothiazepine-4(5H)-one;
3-(hydroxy)-5-[2-[[3,4-dichlorophenyl)ethyl]methylamino]ethyl]-2,3-dihydro-2-(4-methoxyphenyl)-1,5-benzothiazepine-4(5H)-one;
3-(acetyloxy)-5-[2-[[2-(3,4-methylenedioxyphenyl)ethyl]methylamino]ethyl]-2,3-dihydro-2-(4-methoxyphenyl)-1,5-benzothiazepine-4(5H)-one;
3-hydroxy-5-[2-[[2-(3,4-methylenedioxyphenyl)ethyl]methylamino]ethyl]-2,3-dihydro-2-(4-methoxyphenyl)-1,5-benzothiazepine-4(5H)-one;
3-(acetyloxy)-5-[2-[[2-(3-methylphenyl)ethyl]methylamino]ethyl]-2,3-dihydro-2-(4-methoxyphenyl)-1,5-benzothiazepine-4(5H)-one;
3-(acetyloxy)-5-[2-[[2-methoxyphenyl)ethyl]methylamino]ethyl]-2,3-dihydro-2-(4-methoxyphenyl)1,5-benzothiazepine-4(5H)-one;
3-(acetyloxy)-5-[(S)-2-[[2-(3,4-dimethoxyphenyl)ethyl]methylamino]-1-methylethyl]-2,3-dihydro-2-(4-methoxyphenyl)-1,5-benzothiazepin-4(5H)-one;
3-(acetoxy)-5-[(S)-2-[[2-(2,3-dichlorophenyl)ethyl]methylamino]propyl]-2,3-dihydro-2-(4-methoxyphenyl)-1,5-benzothiazepin-4(5H)-one
3-(acetyloxy)-5-[2-[[2-(3,4-dimethoxyphenyl)ethyl]methylamino]ethyl]-2,3-dihydro-2-(4-methoxyphenyl)-1,5-benzothiazepine-4(5H)-one;
3-(acetyloxy)-5-[2-[[2-(3,5-dimethoxyphenyl)ethyl]methylamino]ethyl]-2,3-dihydro-2-(4-methoxyphenyl)-1,5-benzothiazepine-4(5H)-one;
3-(acetyloxy)-5-[2-[[2-(3,4-dichlorophenyl)ethyl]methylamino]ethyl]-2,3-dihydro-2-(4-methoxyphenyl)-1,5-benzothiazepine-4(5H)-one;
3(acetyloxy)-5-[2-[[2-(2,3-dichlorophenyl)ethyl]methylamino]ethyl]-2,3-dihydro-2-(4-methoxyphenyl)-1,5-benzothiazepine-4(5H)-one;
3-(acetyloxy)-5-[2-[[2-(3-methoxyphenyl)ethyl]methylamino]ethyl]-2,3-dihydro-2-(4-methoxyphenyl)-1,5-benzothiazepine-4(5H)-one;
3-(acetyloxy)-5-[2-[[2-(3-dimethylaminophenyl)ethyl]methylamino]ethyl]-2,3-dihydro-2-(4-methoxyphenyl)-1,5-benzothiazepine-4(5H)-one;
3-(acetyloxy)-5-[2-[[2-(3-trifluoromethylphenyl)ethyl]methylamino]ethyl]-2,3-dihydro-2-(4-methoxyphenyl)-1,5-benzothiazepine-4(5H)-one;
3-(acetyloxy)-5-[2-[[2-(3,4-dimethoxyphenyl)propyl]methylamino]ethyl]-2,3-dihydro-2-(4-methoxyphenyl)-1,5-benzothiazepine-4(5H)-one;
5-[2-[[2-(3,4-dimethoxyphenyl)ethyl]methylamino]ethyl]-2,3-dihydro-3-hydroxy-2-(4-methoxyphenyl)-1,5-benzothiazepine-4(5H)-one; or
3-(acetyloxy)-5-[2-[[2-(3,4-dimethoxyphenyl)ethyl]methylamino]propyl]-2,3-dihydro-2-(4-methoxyphenyl)-1,5-benzothiazepine-4(5H)-one.

10. The benzothiazepine of claim 1, wherein said benzothiazepine is the cis isomer.

11. The benzothiazepine of claim 1, wherein said benzothiazepine is cis-3-(acetyloxy)-5-[2-[[2-(3,4-dimethoxyphenyl)ethyl]methylamino]ethyl]-2,3-dihydro-2-(4-methoxyphenyl)-1,5-benzothiazepine-4(5H)-one.

12. The benzothiazepine of claim 1, wherein Ar is phenyl, phenoxy or thiophenoxy substituted by methylenedioxy at adjacent ring carbons.

13. A pharmaceutical composition comprising a benzothiazepine of claim 1 in combination with a pharmaceutically acceptable diluent or carrier.

14. A method of treating angina pectoria which comprises administering to a mammal in need thereof, the pharmaceutical composition of claim 13.

15. A method for treating hypertension which comprises administering to a mammal in need thereof, the pharmaceutical composition of claim 13.

16. A method for preventing the reoccurrence of heart attacks which comprises administering to a mammal in need thereof, the pharmaceutical composition of claim 13.

17. The compound of the following formula (VI):

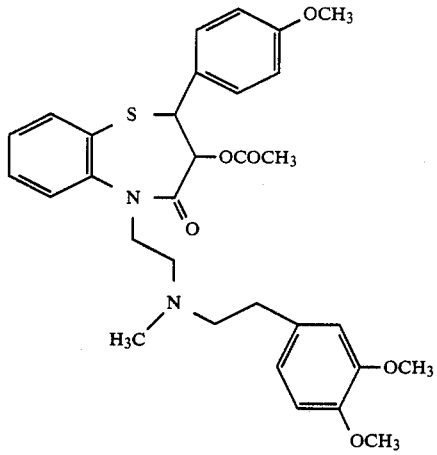

or a pharmaceutically acceptable acid addition salt thereof.

18. The compound of the following formula (VII):

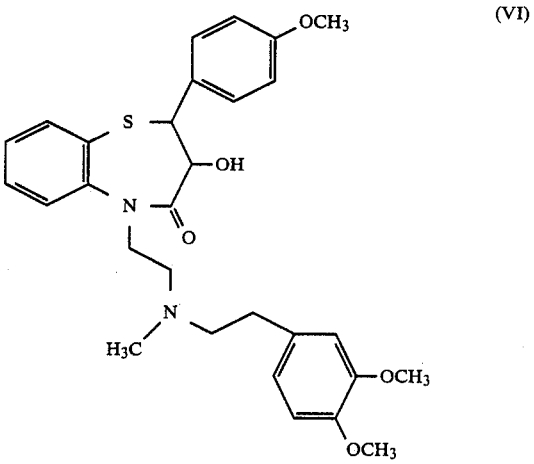

or a pharmaceutically acceptable acid addition salt thereof.

* * * * *

UNITED STATES PATENT AND TRADEMARK OFFICE
CERTIFICATE OF CORRECTION

PATENT NO. : 4,729,994

DATED : March 8, 1988

INVENTOR(S) : John R. Carson

It is certified that error appears in the above-identified patent and that said Letters Patent is hereby corrected as shown below:

Claim 1, column 19, line 11, before "which", insert -- selected from furan, thiophene, pyrrole or pyridine --;

Claim 2, line 18, "$X_1$" should be -- X --;

Claim 2, column 19, lines 36-37, delete "having one nitrogen, sulfur or oxygen atom", and insert therefor -- selected from furan, thiophene, pyrrole or pyridine --;

Claim 7, column 19, line 59, "alkanoyl" should be -- alkoxy --;

Claim 9, column 20, line 41, "3(acetyloxy)" should be -- 3-(acetyloxy) --;

Claim 13, column 21, line 10, after "composition", insert -- useful for treating hypertension, angina or the prevention of heart attacks --; and

UNITED STATES PATENT AND TRADEMARK OFFICE
CERTIFICATE OF CORRECTION

PATENT NO. : 4,729,994

DATED : March 8, 1988

INVENTOR(S) : John R. Carson

It is certified that error appears in the above-identified patent and that said Letters Patent is hereby corrected as shown below:

Claim 13, column 21, line 10, after "comprising", insert -- an effective amount of --.

Signed and Sealed this

Eleventh Day of April, 1989

Attest:

DONALD J. QUIGG

Attesting Officer

Commissioner of Patents and Trademarks